United States Patent
Velez-Rivera

(10) Patent No.: US 9,358,367 B2
(45) Date of Patent: Jun. 7, 2016

(54) CANNULA HOLDER HAVING A GUIDE FOR A STOMACH TUBE

(76) Inventor: Héctor de Jesús Velez-Rivera, Jalisco (MX)

( * ) Notice: Subject to any disclaimer, the term of this patent is extended or adjusted under 35 U.S.C. 154(b) by 0 days.

(21) Appl. No.: 14/238,955

(22) PCT Filed: Aug. 18, 2011

(86) PCT No.: PCT/IB2011/001906
§ 371 (c)(1),
(2), (4) Date: Apr. 16, 2014

(87) PCT Pub. No.: WO2013/024318
PCT Pub. Date: Feb. 21, 2013

(65) Prior Publication Data
US 2015/0018759 A1    Jan. 15, 2015

(51) Int. Cl.
*A61M 25/02* (2006.01)
*A61M 16/04* (2006.01)
*A61M 16/06* (2006.01)

(52) U.S. Cl.
CPC ............ *A61M 25/02* (2013.01); *A61M 16/0409* (2014.02); *A61M 16/0497* (2013.01); *A61M 16/0683* (2013.01); *A61M 2025/022* (2013.01); *A61M 2025/0206* (2013.01)

(58) Field of Classification Search
CPC ............ A61M 25/02; A61M 16/0409; A61M 16/0497; A61M 2025/0206; A61M 16/0683; A61M 2025/022
USPC .............. 604/241–243, 178–180, 307, 890.1, 604/174
See application file for complete search history.

(56) References Cited

U.S. PATENT DOCUMENTS

| | | | |
|---|---|---|---|
| 2,908,269 A | 10/1959 | Cheng | 128/12 |
| 4,249,529 A | 2/1981 | Nestor et al. | 128/207.17 |
| 5,305,742 A * | 4/1994 | Styers et al. | 128/207.17 |
| 5,320,097 A | 6/1994 | Clemens et al. | 128/207.17 |
| 5,806,516 A * | 9/1998 | Beattie | 128/207.17 |
| 6,010,484 A * | 1/2000 | McCormick et al. | 604/174 |
| 6,634,359 B1 * | 10/2003 | Rudy et al. | 128/207.14 |
| 2008/0087281 A1 | 4/2008 | Yang | 128/200.26 |
| 2008/0202529 A1 | 8/2008 | Flory et al. | 128/207.17 |
| 2009/0229616 A1 | 9/2009 | Liland | 128/207.14 |

OTHER PUBLICATIONS

International Search Report mailed Mar. 29, 2012 in corresponding PCT International Application No. PCT/IB2011/001906.
International Preliminary Report on Patentability dated Mar. 3, 2014 for corresponding PCT International Application No. PCT/IB2011/001906.

* cited by examiner

*Primary Examiner* — Kami A Bosworth
*Assistant Examiner* — Hamza Darb
(74) *Attorney, Agent, or Firm* — Ostrolenk Faber LLP

(57) ABSTRACT

The invention relates to a cannula holder having a guide for a stomach tube, which consists of a main body or mask; a male-female type of holder attached to said main body or mask, which provides graduated support for an endotracheal cannula; a support substrate that is attached to the rear part of the main body or mask; and an extensible band or strap, the ends of which are attached to each of the lateral ends of the main body or mask, wherein said extensible band or strap extends around and behind the head of the patient or user to keep the cannula holder having a guide for a stomach tube in place. The invention also relates to the fact that the holder, in addition to being used for holding an endotracheal cannula, can be used to hold any other medical device used in connection with the oral airways, such as a laryngeal mask.

11 Claims, 6 Drawing Sheets

CANNULA HOLDER HAVING A GUIDE FOR A STOMACH TUBE

CROSS-REFERENCE TO RELATED APPLICATIONS

The present application is a 35 U.S.C. §§371 national phase conversion of PCT/IB2011/001906, filed Aug. 18, 2011, the contents of which are incorporated herein by reference. The PCT International Application was published in the Spanish language.

TECHNICAL FIELD

The instant invention is related to those techniques applied to the manufacture and design of mechanism used for holding and fastening auxiliary devices employed in therapeutic and surgical procedures, and more particularly, the invention is related to a cannula holder having a guide for a stomach tube.

BACKGROUND OF THE INVENTION

There are two main devices for supplying and exhausting gases from the airways of a patient, for example, during a general anaesthesia procedure in surgery, they are the endotracheal cannula and the laryngeal mask.

The endotracheal cannulas are artificial airways used for maintaining permeable the upper airways and avoiding the tongue obstructs the airways, then adequate ventilation and oxygenation is provided to the patient while secretions of the patient are controlled when tubing is applied to the patient. The endotracheal cannula is a tube that is introduced to the mouth or the trachea avoiding the closing of the last and maintaining the ventilation or breathing of the patient, the endotracheal cannula is used when the airways are handled in short times. The neonates with respiratory difficulties require mechanic-ventilatory medical assistance through the endotracheal tube; so that, it is very important to have in mind the position of the endotracheal tube.

On the other hand, the laryngeal mask is used for controlling airways in adults and children under difficult situations of the airways as well as in different anaesthetic and surgical procedures. The laryngeal mask consists of a silicon tube connected at a 30° angle to a rubber mask that is slightly concave and has an inflatable rubber balloon.

The laryngeal mask has the advantage of being best tolerated in lower levels of anaesthesia in comparison with the endotracheal cannula; in addition the laryngeal mask causes fewer traumatic risks such as laryngeal pain and post operatory aphonia.

From the above, it is very desirable that the means that supplies and exhausts the gases from the airways of the patient remain unmovable with respect to the anatomy of the patient when the tubes are placed in the patient during an urgent surgical operation is carried out, or, in cases when artificial breathing is required for the patient when the same is on bed. Moreover, the patient requires certain liberty of movement and it is necessary avoiding the conducts to be obstructed in order to facilitate the breathing of the patient. In this regard, during the placement of the endotracheal cannula or the laryngeal mask, the same are usually inserted through the mouth of the patient, so that it is very important keeping the endotracheal cannula or the laryngeal mask fastened all the necessary time.

In the prior art, there are some devices for holding a cannula, which have been designed for holding the endotracheal cannula to the anatomy of a patient, one prior art device is disclosed in U.S. Pat. No. 2,908,269, this patent refers to a device for fixing the endotracheal cannula comprising a bite block which is inserted in the mouth in order to keep the jaws spread apart in a sufficient distance to permit the insertion of a resilient tube into the mouth and down the throat or trachea, depending upon the particular needs, without it being necessary to disturb the position of the bite block in the month during either insertion or removal of the resilient tube. Even though that this device is fixed in the mouth of a patient, wherein the cannula may be inserted or removed of the mouth without changing the position of said holder, the diameter of the cannula which is held in the device of this patent is limited to only one diameter, it is not possible varying the dimension of the aperture for holding cannulas with a different diameter according to the size of the user, in addition, the device has grooves and holes between the mouth and the plate of the holder in which biological material may be accumulated infecting the patient.

On the other hand, U.S. Pat. No. 4,249,529 discloses an endotracheal tube holder having a body which is secured by a pair of non-stretchable, head encircling straps to overlie the patient's mouth and portions of the cheeks. The straps, which are adapted to extend, one above and the other below, the patient's ears, have one-way tightening adjustability by pawl action. The body is integrally moulded to incorporate a quick-acting clamp having three integral hinges, one hinge pivotally connecting a pair of jaws of the clamp and the other two hinges supporting the jaws from resilient arms for snap-action between open and closed positions. The clamp is operative to secure or release the endotracheal tube while the straps retain the body in position on the mouth against dislodgment. Nevertheless the object of this device is facilitating the access to the mouth of the patient with an endotracheal cannula to be fixed, the device fails to provide a aperture with variable dimension, so that the device is only used when it is available an endotracheal cannula with a specific diameter for this device.

Likewise, in the prior art, it is found U.S. Pat. No. 5,320, 097 disclosing an endotracheal tube holding and securing device, which includes two identical hook-shaped members forming a "C" shaped gripper used for holding the endotracheal tube. Each hook-shaped member comprises a groove and a pin that allow longitudinal displacement of one member with respect to the other, thus varying the diameter of the "C" shaped gripper when there is a relative movement of one member to respect the other. Each of the hook members has straight an upper surface and a lower surface on which the lips of the user are positioned. In order to keep the holder it its original position, a fabric strap is provided in each of the ends of the hook members, the extension of the strap is adjusted to the diameter of the head of the user.

However, the holder disclosed in the previous paragraph fails to provide a textured surface in the inner part thereof in which the cannula may be in contact for reaching a firm holding thereof, so that unwanted displacements of the cannula may occur. In addition, when the holder is place, there is a possibility that one of the bolts remains jammed avoiding the relative movement between the members so that the use of the device is not possible any more. Another disadvantage of said holder is related with the fact that the size of the hooks is constant, in addition, the form of each hook is not ergonomic that provokes nuisance and lesions in the mouth of the patient that uses the holder.

Now, in US Patent Application 2008/0202529, it is disclosed an endotracheal tube holder including a base with a tube-securing block, the base is supported on the lips of the patient and is held to the head of the patient with the aid of bands. In order to maintain the cannula in place, a U-shaped clip is engaged in the block of the base. In addition, in order to avoid unwanted movements of the clip with respect to the block, both of them have edges provided with teeth which avoid said unwanted movement. In a further embodiment, said holder has an anti-bite block, which avoids teeth of the patient bite the cannula affecting the performance of the device. However, the holder of this patent application allocates the cannula at one side of the mouth of the patient increasing the risk of ulcerating the patient. Moreover, the holder has elements that are time-consuming when the holder is assembled, this means that the elements may not be placed at a first attempt; in addition the personal should have advanced skills for assembling the holder.

Other example of a cannula holder of the prior art is that known as the "Thomas" model endotracheal cannula holder fabricated by the company "Laerdal", this model comprises an arc-shaped main body made from a rigid polymeric material having a central entrance by which the endotracheal cannula is introduced. In order to hold the cannula, this model uses a tightening screw that is located at one side of the arch, so that the screw should be rotated several times by the user in order to get a secure holding of the cannula. However, the cannula holder has the drawback that the screw pressures the cannula in order to maintain the same in place avoiding its movement; this mechanism may deform the cannula obstructing the air flow to the patient. Moreover, if the user that is placing the cannula holder in the mouth of the patient is not aware of the screw position with respect to the cannula, the last may be broken due to the concentration of axial forces at one point of the cannula.

From all the above previously disclosed, the holders of the prior art have surfaces that are in contact with the cannula that lacks of a textured surface to be held leading to an unsatisfying adjustment of the cannula to the patient. Moreover, the prior art devices fails to facilitate the cannula to be repositioned if the same is moved, on the other hand the comfort of the device is not taken into account, particularly when the holder is in contact with the skin or mucosa of the patient.

SUMMARY OF THE INVENTION

The instant invention is related with a cannula holder having a guide for a stomach tube, the cannula holder comprises, in general, a main body or a mask; holding means rotary mounted to said main body or mask; a support substrate that is fixed to the rear surface of the main body or mask; and an extensible strap or band joined to the main body or mask, wherein the band extends around and behind the head of a patient in order to keep the cannula holder of the instant invention in place.

The main body or mask has an arc shape and has a plurality of perforations over its surface, each of said perforations has a shape, size and location on the mask that is different with respect to the other perforations. Among said perforations, there is a pair of channels having an enlarged eyelet shape, each of said channels is located at one of the lateral sides of the main body or mask, the function of each channel is receiving one of the ends of the extensible strap or band.

In addition, the main body or mask has a tunnel that allows an endotracheal cannula or laryngeal mask to be inserted to the mouth of the patient. The tunnel has an entrance which preferably has an inverted-V shape; the tunnel transversally runs from said entrance to the rear part of mask. The tunnel, besides functioning as a guide for the endotracheal cannula, also functions as a bite protector in order to avoid the patient bites the cannula.

A flange or protrusion is provided next and above to the aperture or entrance, the flange protrudes outwardly from the external surface of the mask with a length that is preferably twice the width of the mask; the flange looks like an inverted-V.

From the plurality of perforations that are provided in the mask, there is an opening that is laterally located (preferably at the right side) with respect to the entrance, the function of the opening is allowing a stomach aspiration tube to be inserted. Moreover, an anchor port is provided at the opposite side of the aperture and next to the entrance, the anchor port comprises a pair of perforations, the first one is a circular perforation that is immediately located next to the entrance; the second one is a female perforation having a "C" shape located at the left side and next to the circular perforation. The C-shaped female perforation includes a plurality of teeth on one of its edges, said plurality of teeth is preferably provided at the distal edge of the female perforation.

On the other hand, the support substrate preferably has an oval form and includes upper and lower arcs that exceed the size of the mask at the upper part and the lower part thereof respectively in order to provide comfort to the user. The support substrate also has right and left side arcs and, both coinciding with the proximal ends of the eyelet-shaped channels that are located at the lateral sides of the mask. Said support substrate has a first perforation with an spearhead shape which couples with the upper surface of the tunnel of the mask; said first perforation has an inlet running from the base of the first perforation until the lower arc so that a gap is formed in which the endotracheal cannula may be inserted. In addition the support substrate has a second perforation laterally placed with respect to the first perforation; the second perforation has an isosceles-triangular form with rounded corners, so that the second perforation coincides with the opening of the mask in order to allow the gastric tube to be easily inserted.

The holding means are asymmetrical and comprises: a first support zone located at the left side of the holding means, the first zone includes two concave surfaces; a second support zone preferably located at the opposite side with respect the position of the first zone; the second support comprises an external wall having a concave surface.

In addition, an arm runs from the inner face of the second support zone towards the upper part of the first support zone, the arm has a crown located on its upper end, the crown includes a circular hole, the diameter and width of the internal wall of the circular hole are smaller with respect to the diameter and width of the crown, so that a step is formed in the front and rear faces of the crown. Finally a pivot is housed in the front step and a tightening washer is housed in the rear step.

The first support zone also includes a male protrusion that is located at the upper and rear part of the first support zone, the male protrusion is provided with a plurality of teeth at one of its side faces, the plurality of teeth matches with the plurality of teeth located at the distal end of the C-shaped female perforation of the anchor port, so that a graduated regulation is formed avoiding unwanted movements of the holding means are avoided and maintaining the pressure that is exerted on the endotracheal cannula.

With the purpose of maintaining the holding means coupled to the mask a pivot is used, the same has a stepped cylindrical form having three sections longwise, a lower section, a middle section and an upper section. In addition for the coupling of the holding means to the mask a tightening washer is used, of which its central perforation has a diameter that is slightly smaller than the diameter of the lower section of the pivot, whereby the tightening washer is received under pressure in the pivot, provoking a click-type closure with a radial projection located at the lower section of said pivot.

In order to avoid unwanted movements of the holding means, as backwards movements; the plurality of teeth located at the second perforation of the anchor port is downwardly inclined so that only an anticlockwise rotation is allowed. However, if the user needs to withdraw the cannula or placing a new one, it is necessary applying a torque as well as axial forces on the concave surfaces of the first and second support zones. In this manner, it is created a temporal separation between the second plurality of teeth located in the male protrusion of the first support zone and said plurality of teeth of the C-shaped female perforation so that a relative movement is allowed in clockwise direction.

The endotracheal cannula or the laryngeal mask is inserted through the separation between the aperture of the mask and the support substrate in direction to the entrance remaining located in said entrance and being protected by the protector. In order to avoid the movement of the cannula holder with respect to the mouth of the patient once the devices is placed, the ends of the extensible band or strap are placed in each of the lateral sides of the mask and more specifically at each of the eyelet-shaped channels, the band being positioned around the head of the user.

BRIEF DESCRIPTION OF THE DRAWINGS

Novel aspects featured by the present invention shall be set forth in connection with the appended claims. Nevertheless, the invention itself shall be better understood regarding its structure and function, as well as other objects and advantages of the same, with the following detailed description of a preferred embodiment thereof, when read in conjunction with the appended figures, in which

OBJECTS OF THE INVENTION

Having in mind the prior art drawbacks, an object of the instant invention is to provide a cannula holder device having a guide for a stomach tube, wherein the construction and design thereof is notably simple but highly effective for allowing a firm holding of an endotracheal cannula without affecting the structural rigidity and the performance thereof.

Another object of the instant invention is to provide a cannula holder device having a guide for a stomach tube that allows an easy and fast holding of the endotracheal cannula using for this purpose holding means allowing cannulas of distinct diameter to be inserted.

Moreover, an additional object of the instant invention is to provide a cannula holder device having a guide for a stomach tube having a bite protector for impeding the user or patient bites the cannula affecting the performance of the device.

One more object of the invention is to provide a cannula holder device having a guide for a stomach tube that includes a guide for a gastric aspiration tube; the device allows secretions to be easily withdrawn without affecting the performance of the device.

Yet, other object of the instant invention is to provide a cannula holder device having a guide for a stomach tube including a support substrate that is placed over the mouth of a user; the substrate avoids provoking lacerations to the user.

A further object of the instant invention is providing a cannula holder device having a guide for a stomach tube that may be fixed to the head of a patient by means of an extensible band or strap that surrounds the head of the user, so that the device can not be moved, even in the case the patient is being suddenly moved.

An addition object of the instant invention is providing a cannula holder device having a guide for a stomach tube that besides allows an endotracheal cannula to be held, also allows any medical device used for the airways of a patient to be also held, such a laryngeal mask and other similar devices.

DETAILED DESCRIPTION OF A PREFERRED EMBODIMENT OF THE INVENTION

Figure 1:
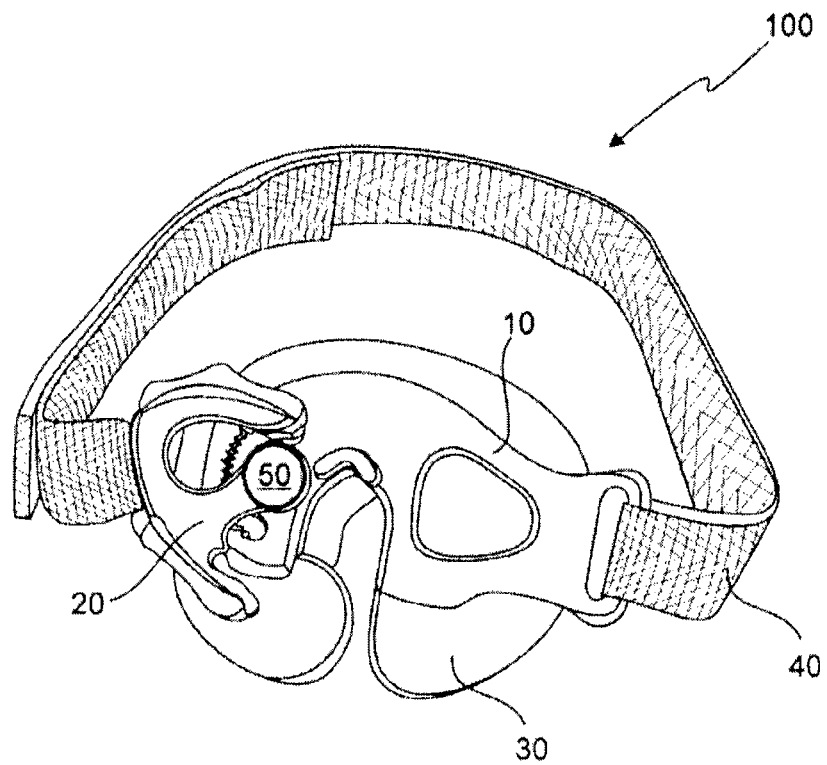
FIG. 1 is a frontal and right side perspective view of a cannula holder device having a guide for a stomach tube, the device being constructed in accordance to the principles of a particularly preferred embodiment of the instant invention.
Figure 2:
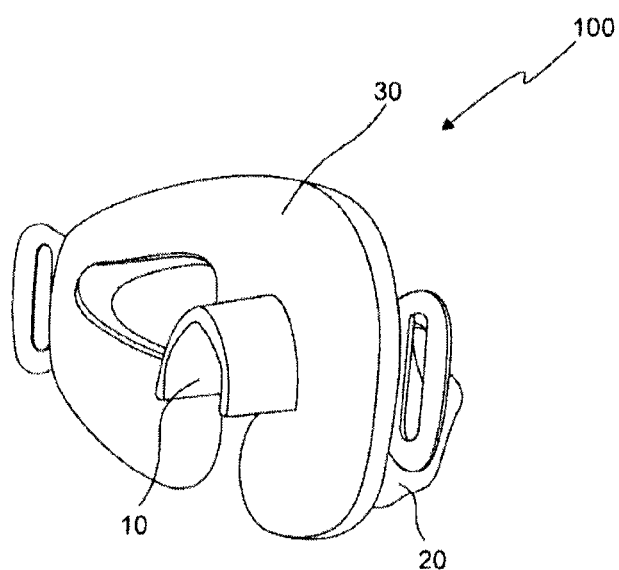
FIG. 2 is a rear and left side view of the cannula holder device having a guide for a stomach tube without the extensible band that surrounds the head of a patient.

Reference is made to the attached drawings, more particularly to FIGS. 1 and 2 in which it is illustrated a cannula holder device 100 having a guide for a stomach tube, the device built in accordance with a particularly preferred embodiment of the instant invention, this embodiment should be considered illustrative but not limitative of the invention. The cannula holder device 100 comprises, in general terms, a main body or mask 10; holding means 20 pivotally coupled to said main body or mask 10; a support substrate 30 that is fixed to the rear surface of the main body or mask 10; and an extensible strap or band 40, the ends of this strap are fixed to the main body or mask 10, the strap extends around and behind the head of a patient in order to keep the cannula holder device with a guide for a stomach tube of the instant invention in place.

Figure 3:
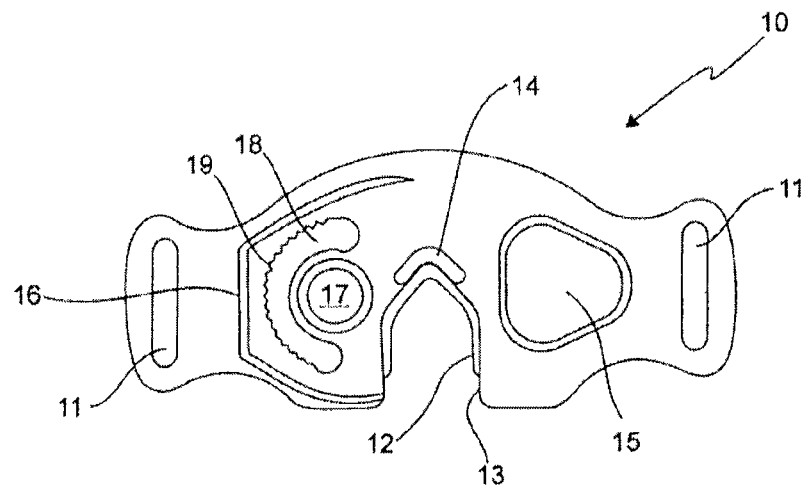
FIG. 3 is a frontal view of the main body or mask that is part of the cannula holder device having a guide for a stomach tube illustrated in FIG. 1.
Figure 4:
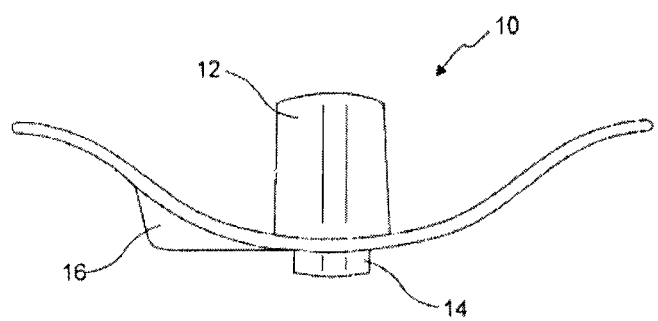
FIG. 4 is a top plan view of the main body or mask shown in FIG. 3.

Now, reference is made to FIGS. 3 and 4 of the appended drawings, in said figures it is shown the main body or mask 10 which has an arc shape in order to be coupled to the anatomy of the face of a patient. The mask has a plurality of perforations or holes distributed over its surface, each perforation has a purpose in the main body or mask 10, particularly, each of said perforations has a shape, size and a particular location over the masks that is different with respect to other perforation. Among said perforations, there is a pair of channels 11 having an enlarged eyelet form, each of said channels 11 is located at one of the lateral sides of the main body or mask 10, the function of each of the channels is receiving one of the ends of the extensible strap or band 40.

In addition, the main body or mask 10 has a tunnel 12 located at the middle of lower half of the mask, the tunnel allows an endotracheal cannula or laryngeal mask to be inserted to the mouth of the patient when the holder device 100 of the instant invention is in use. The tunnel 12 has an aperture or entrance 13 having preferably an "inverted-V" shape, the tunnel 12 transversally runs from said entrance 13 to the rear part of mask 10, the tunnel has a length that is preferably equal to the transversal distance between the crest of the arc and the lateral ends of the arc-shaped mask as it can be observed in FIG. 4 of the appended drawings. In a further embodiment, the cannula holder device 100 is also used for holding a laryngeal mask.

Besides functioning as a guide for the endotracheal cannula, the tunnel 12 also functions as a bite protector in order to avoid the direct contact of the teeth of the patient with said endotracheal cannula, whereby the patient is avoiding biting the endotracheal cannula provoking its rupture. A flange or protrusion 14 is centrally provided above the aperture or entrance 13, the flange protrudes outwardly from the external surface of the mask 10, the flange has a length that is preferably twice the width of the mask 10, the flange 14 has a peripheral contour with the same shape as the central part of the entrance 13, that is to say, the flange 14 has an inverted-V shape.

From the plurality of perforations that are provided over the mask 10, there is an opening 15 that is laterally located at the right side of the entrance 13, the function of the opening 15 is allowing the insertion of a stomach aspiration tube (not shown in drawings), the opening 15 preferably has an isosceles triangle form with rounded corners, the base of the triangle is next to the entrance 13.

Moreover, an anchor port 16 is provided next to the entrance 13 and at the opposite side with respect the opening 15, the anchor port 16 comprises a pair of perforations, the first one is a circular perforation 17 that is immediately located next to the entrance 13; the second one is a C-shaped female perforation 18 located at the left and next to the circular perforation 17, in such a manner that the circular perforation 17 is centrally located at the middle of the C-shaped female perforation 17. The female perforation is provided with a plurality of teeth 19 at one of its walls, preferably at the distal wall. The circular perforation 17 and the female perforation 18 function in conjunction with the holding means 20 in order to hold the endotracheal cannula or the laryngeal mask.

The anchor port 16 has a perimeter wall that surrounds the female perforation 18 in addition, the perimeter wall protrudes above the surface of said anchor port 16 in order to provide additional support to the holding means holding and allowing them freely rotate.

It is worth mentioning that all the edges and borders of the mask 10 are rounded in order to avoid the patient or the person who places the device 100 on the patient suffer lacerations in comparison if the mask is provided with shaped edges.

Figure 5:
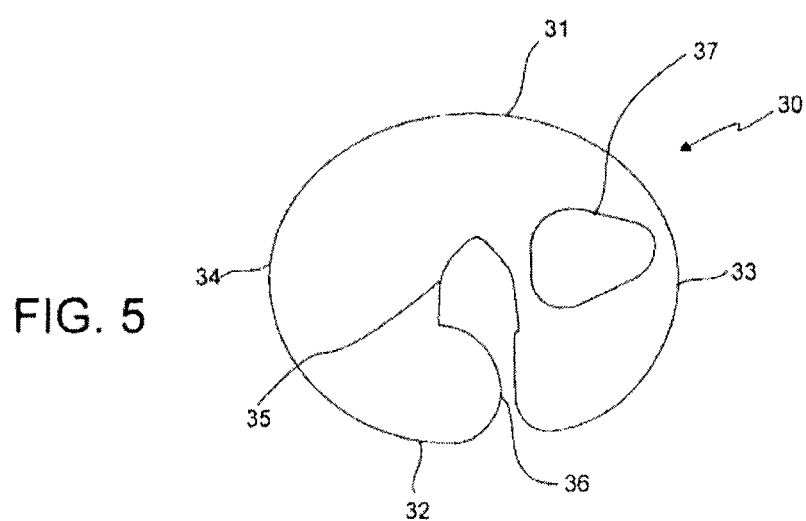
FIG. 5 is a frontal view of the support substrate that is part of the cannula holder device having a guide for a stomach tube of the instant invention.
Figure 6:
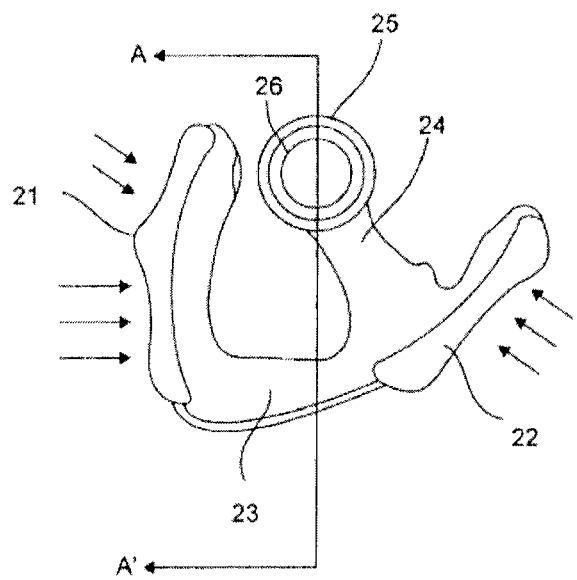
FIG. 6 is a frontal view of the holding means that are part of the cannula holder device having a guide for a stomach tube of the instant invention.
Figure 7:
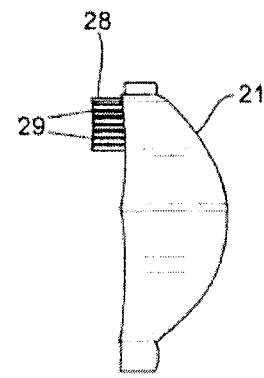
FIG. 7 is a left side view of the holding means shown in FIG. 6.

Specific reference is make to FIG. 5 of the appended drawings, in which it is observed that the support substrate preferably has an oval form, having upper and lower arcs 31 and 32 that protrudes upwardly and downwardly with respect the size of the mask, respectively, said arcs provide more comfort to the user when the cannula holder device is used for many time. The support substrate also has right and left side arcs 33 and 34, respectively, both coincide with the proximal ends of the eyelet shaped channels 11 that are located at the lateral sides of the mask 10 so that said left and right arcs do not interfere with the extensible band 40. Said support substrate 30 has a first perforation 35 having a spearhead form which couples with the upper surface of the tunnel 12 of the mask 10, the first perforation 35 has an inlet 36 running from the base of the first perforation 35 until the lower arc 32 so that a gap is formed in which the endotracheal cannula or the laryngeal mask may be inserted. In addition the support substrate has a second perforation 37 that is laterally located with respect to the first perforation 35; the second perforation has an isosceles triangular form with rounded corners, so that the second perforation 37 coincides with the opening 15 of the mask 10 in order to allow the gastric tube to be easily inserted.

Reference is made to FIGS. 6-13 of the appended drawings, in which it is shown the holding means 20 that are pivotally mounted to the mask 10 by means of the anchor port 16; the holding means are asymmetrical and comprises; a first support zone 21 located at the left side of the holding means; the first support zone 21 includes two concave surfaces; a second support zone 22 located at the opposite side with respect the first support zone 21; the second support zone comprises an external wall having a concave surface. In order to provide more structural rigidity to the holding means, said first and second support zone 21 and 22 are interconnected by a rib 23.

Figure 8:
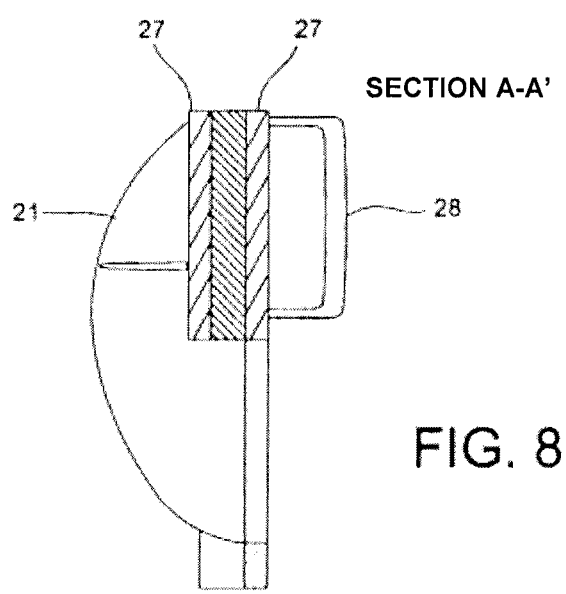
FIG. 8 is a transversal section view taken along the line A-A' of FIG. 6.

In addition, an arm 24 runs from the inner face of the second support zone 22 towards the upper part of the first support zone 21, the arm 24 has a crown 25 located at its upper end, the crown 25 includes a circular hole 2, the internal wall of which having a diameter and width that are smaller with respect to the diameter and width of the crown 25, so that a step 27 is formed on the front and rear faces of the crown 25 as it is shown in FIG. 8 of the appended drawings, the step 27 allows a pivot 50 to be housed in the front face and a tightening washer is housed in the rear face, respectively.

The first support zone 21 also includes a male protrusion 28 that is located at the upper and rear part of the first support zone, the male protrusion 28 is provided with a plurality of teeth 29 on one of its side faces, said plurality of teeth 29 engages with the plurality of teeth 19 provided at the distal wall of the C-shaped female perforation 18 of the anchor port 16, so that a graduated tightening is formed avoiding the holding means to be moved, in addition pressure is exercised on the endotracheal cannula, in other words, it is avoided any movement of said endotracheal that may feel the patient uncomfortable.

Figure 9:
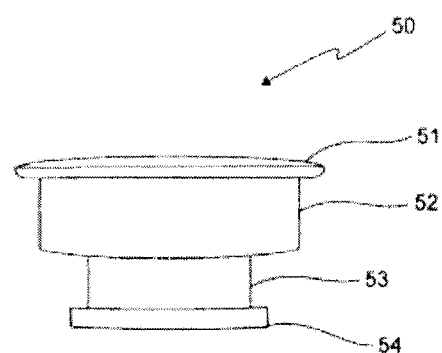
FIG. 9 is a left side view of the pivot that is part of the holding means that are part of the cannula holder device having a guide for a stomach tube of the instant invention.
Figure 10:
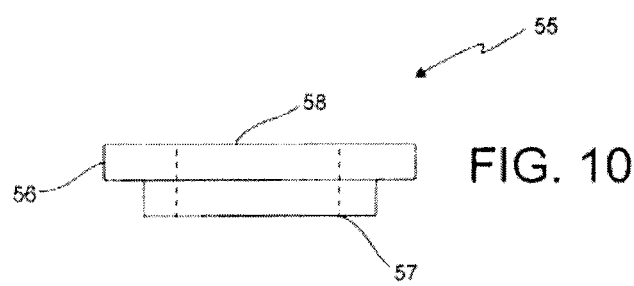
FIG. 10 is a lateral view of a tightening washer that is part of the holding means of the cannula holder device having a guide for a stomach tube of the instant invention.
Figure 11:
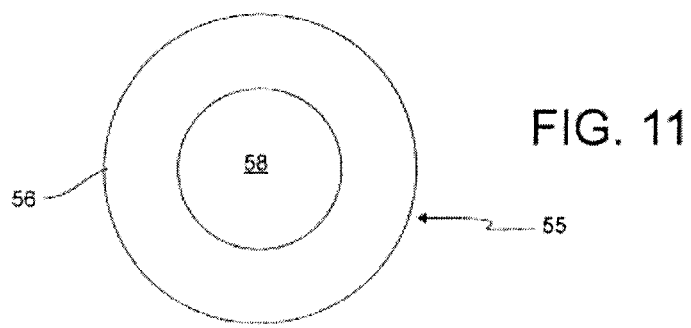
FIG. 11 is a frontal view of the tightening washer shown in FIG. 10.
Figure 12:
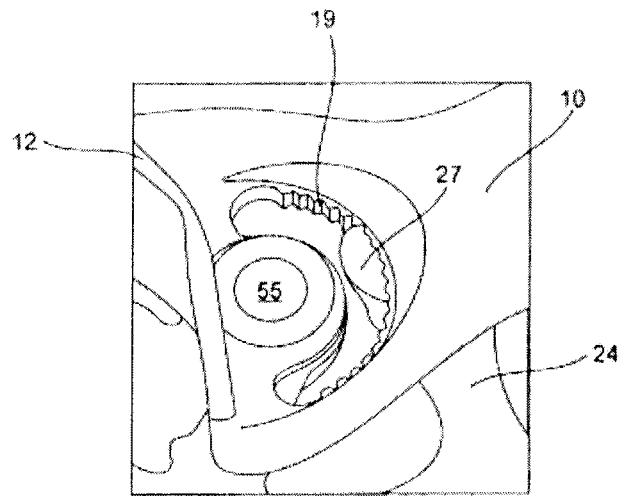
FIG. 12 is an enlarged partial perspective view that shows the coupling of the holding means to the main body or mask in order to form the cannula holder device having a guide for a stomach tube of the instant invention.

In order to maintain the holding means 20 and the mask 10 coupled each to other, a pivot 50 is used, the pivot preferably has a stepped cylindrical form, so that it comprises three sections lengthwise with different diameter, as it may be observed in FIG. 9 of the appended drawings, said sections are: an upper section 51 with the largest diameter, the end of which having a semi-spherical shape; a middle section 52;

and a lower section 53 that has the smallest diameter along the pivot and is provided with a radial projection 54 at its lower end.

In addition, for coupling the holding means 20 to the mask 10 a tightening washer 55 is used, the washer has a stepped shape defining an upper portion 56 and a lower portion 57, wherein said upper portion has a largest diameter with respect to the diameter of the lower portion 57, nevertheless the diameter of the upper portion 56 is equal to the diameter of the upper section 51 of the pivot 50. While the diameter of the central perforation 58 of the tightening washer 55 is smallest with respect to the diameter of the lower section 53 of the pivot 50, whereby said tightening washer 55 is introduced under pressure in said pivot 50, in addition a "click" type closure is made with the radial projection 54 provided in the lower section 53 of the pivot 50.

Figure 13:
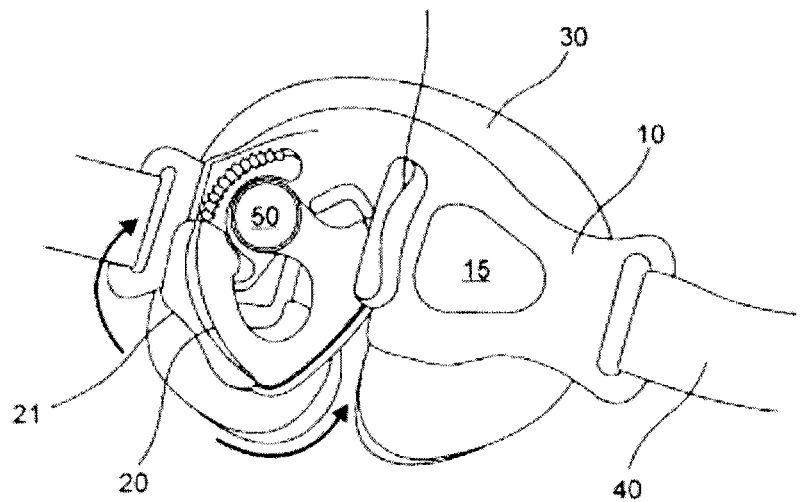
FIG. 13 is a perspective frontal view of the cannula holder device shown in FIG. 1, in which the holding means may rotate in a clockwise an anti-clockwise direction.

Now reference is made to FIG. 13, in which, it is observed that the first support zone 21 and the second support zone 22, which are provided in the holding means 20, function as a base or platform for the fingers as well as they allow the holding means freely rotate both in a clockwise direction and in an anti-clockwise direction in order to open or close the inlet of the support substrate gap and the entrance 13 provided at the frontal part of the mask 10 on function of the diameter of the cannula diameter that that is inserted.

Once the endotracheal cannula has been inserted in the entrance 13 of the main body or mask 10, the cannula remains in place by the action of the holding means 20, which as it was previously mentioned rotates over the pivot due to the rotation axis provided by the pivot 50 and the tightening washer 55, so that said holding means 20 has the function of holding and pressuring the endotracheal cannula having the advantage that the holding means are adaptable for receiving cannulas of different diameter due to the rotation movement thereof.

In order to avoid unwanted movements of the holding means 20, as well as avoid to be regressed, the plurality of teeth 19 provided on the C-shaped female perforation 18 has a certain downwardly inclination so that the rotation movement is only allowed in an anti-clockwise direction. On the other hand, if the user requires to withdraw the inserted cannula or introduce a new one, it will be necessary apply a torque and axial forces over the concave surfaces of the first and second supporting zones 21 and 22, whereby it is created a temporal distancing between the plurality of teeth 29 provided at the male protrusion 28 of the first support zone 21 and said plurality of teeth 19 of the female perforation 18, allowing a relative movement in a clockwise direction.

Figure 14:
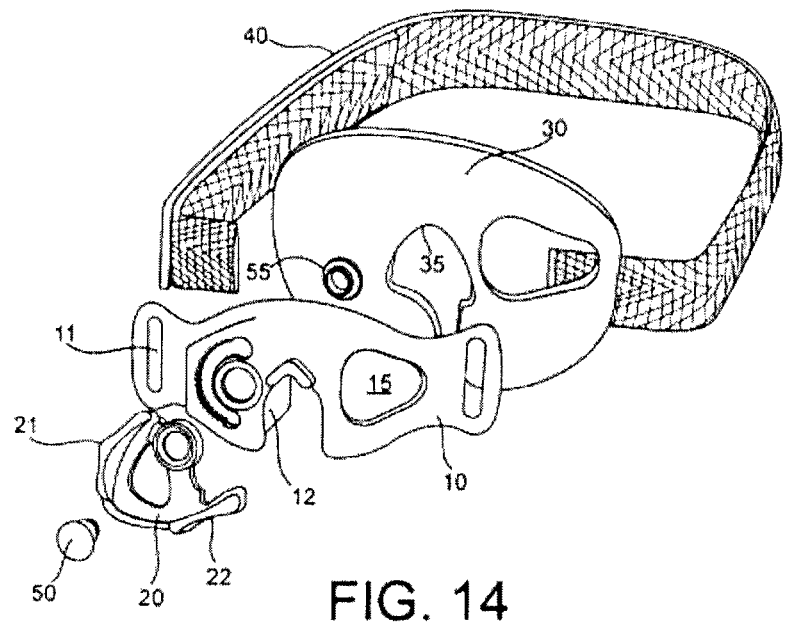
FIG. 14 is an exploded upper perspective view of the cannula holder device having a guide for a stomach tube shown in FIG. 1.

Regarding FIG. 14 of the appended drawings, in said figure it may be observed all the components of the cannula holder device 100 according to the particularly preferred embodiment of the invention of the invention currently disclosed.

Figure 15:
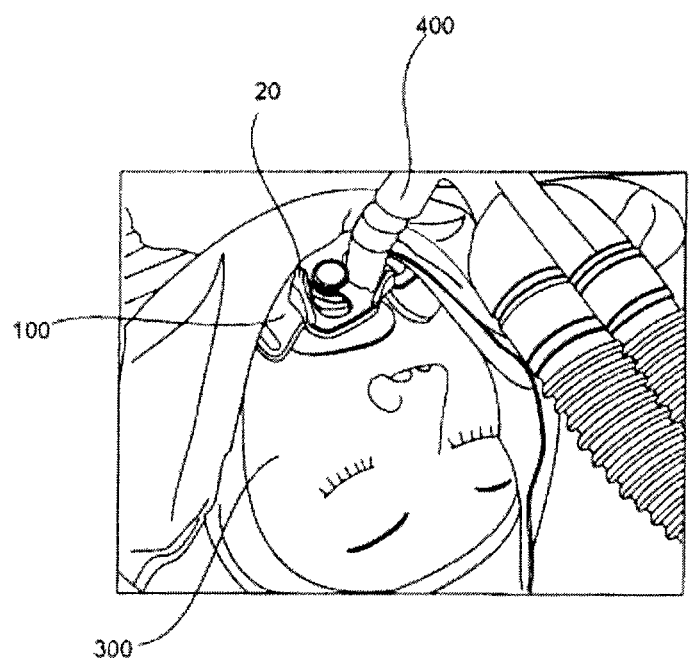
FIG. 15 is and schematic view in order to illustrate the use of the cannula holder device having a guide for a stomach tube of the instant invention along with a laryngeal mask in a patient.

With respect to FIG. 15 of the appended drawing, it is observed a patient 300 using the cannula holder device 100 of the instant application, the device is particularly useful for those cases in which an endotracheal cannula or any other device useful for the airways requires to be held such as a laryngeal mask 400.

Once the endotracheal cannula or the laryngeal mask 400 is introduced trough the mouth of the patient, they are keeping in place by the holder device of the instant invention.

The endotracheal cannula or the laryngeal mask 400 is inserted trough the entrance 13 of the mask 10 and the inlet of the support substrate 30 towards the entrance 13 in order to be placed therein and being protected by the flange 14, which avoids the patient directly bites the endotracheal cannula, deforming the same and affecting the performance thereof.

In order to impede any relative movement of the cannula holder device with respect the mouth or face of the patient 300 once the device is placed; in each of the ends of the mask, particularly in both eyelet-shaped channels 11, the ends of the extensible strap 40 are placed, the strap being collocated around the head of the user.

Once the cannula holder device 100 has been placed into the mouth of the user 300 as well as the endotracheal cannula or the laryngeal mask 400 are in place, an stomach tube may be inserted through the opening 15 of the mask 10, the function of the tube is removing any secretion produced by the patient 300.

The fabrication materials of the cannula holder device should be hypoallergenic and non-toxic materials. More particularly, the construction materials of the main body 10 and the holding means 20 are selected from the group consisting of polystyrene, polyethylene, polypropylene, ABS, and other rigid polymers. While the construction material of the support substrate 30 is selected from foamed EVA, foamed polyethylene, rubber and latex. The extensible band or strap 40 is made from nylon materials.

It will be evident for any skilled in the art that the previously disclosed embodiment of the cannula holder device having a guide for a stomach tube, that has been illustrated in the appending drawings is only illustrative but not restrictive of the instant invention since several modifications of the same are possible without departing the scope of the invention such as the modification of the peripheral contour of the aperture of the mask, the position of the eyelet shaped channels, the geometric form of the elements of the holder, the material for the construction of the device, etc. Therefore, this invention should not be considered as limited except for what it is required by the prior art and by the scope of the appended claims.

What is claimed is:

1. A cannula holder device having a guide for a stomach tube, the device comprising:
   a mask having a tunnel for allowing insertion of an endotracheal cannula and an opening for insertion of the stomach tube, the mask having a rear surface and lateral sides;
   holding means coupled to the mask;
   a support substrate that is fixed to the rear surface of the mask; and
   an extensible strap having ends, each end being fixedly attached to a respective lateral side of the mask;
   wherein the holding means comprises:
   a first support zone located at one side of the holding means and including two concave surfaces and an upper part;
   a second support zone located at an opposite side located opposite to said one side, the second support zone comprising an external wall having a concave surface and an internal face;
   a rib connecting the first support zone with the second support zone, wherein the rib provides structural rigidity to the holding means; and
   an arm running from the internal face of the second support zone towards the upper part of the first support zone, the arm having an upper end and a crown located at the upper end, the crown including a circular hole.

2. A cannula holder device having a guide for a stomach tube, according to claim 1, wherein the crown has a rear face, a front face, a diameter, and a width, and the circular hole has a diameter that is smaller than the diameter of the crown, and a width that is smaller than the width of the crown to define, at the rear face and the front face of the crown, a step in which a pivot is housed at the frontal face and a tightening washer is housed at the rear face.

3. A cannula holder device having a guide for a stomach tube according to claim 2, wherein the pivot is a stepped cylindrical pivot to keep the holding means coupled to the mask, the pivot having an upper section, a middle section, and a lower section having a smallest diameter in the pivot and is provided with a radial projection at its lower end, the tightening washer having a stepped section defining an upper portion and a lower portion, the upper portion having a largest diameter with respect to the lower portion but having a same diameter as a diameter of the upper section of the pivot, the diameter of the central perforation of the tightening washer being smaller than the diameter of the lower section of the pivot, whereby the tightening washer enters under pressure in the pivot, generating a click-type closure with the radial projection located in the lower portion of the pivot.

4. A cannula holder device having a guide for a stomach tube according to claim 3, wherein the holding means pivotally rotates over a rotation axis provided by the pivot and the tightening washer.

5. A cannula holder device having a guide for a stomach tube according to claim 4, wherein the holding means freely rotate clockwise and anti-clockwise to open or close the entrance of the tunnel when fingers of a user are placed on the first support zone and the second support zone located on the holding means, whereby the device is allowed to receive cannulas of different diameters.

6. A cannula holder device having a guide for a stomach tube according to claim 4, wherein application of torque and axial forces over the concave surfaces of the first and the second support zones of the holding means, respectively, create a temporal spacing between the plurality of teeth located on the male protrusion of the first support zone and the plurality of teeth of the C-shaped female perforation so that a movement in a clockwise direction is allowed to permit withdrawal of the cannula and placement of a new cannula.

7. A cannula holder device having a guide for a stomach tube according to claim 1, wherein the tunnel is located at a middle of a lower half of the mask, wherein the opening for the stomach tube is laterally located with respect to the tunnel which also includes an entrance, and wherein the mask also includes a flange that is centrally located and adjacent to an upper part of the entrance, the flange extending from a surface of the mask to a front part thereof and having a length that is twice a width of the mask, the flange having an inverted V shape.

8. A cannula holder device having a guide for a stomach tube according to claim 1, wherein the mask also includes an anchor port that is located at an opposite side with respect to the opening for the stomach tube, the anchor port including a pair of perforations, a first one of the perforations is a circular perforation and is located immediately next to an entrance of the tunnel, while a second perforation of the perforations is a female C-shaped perforation that is located next to the circular perforation, so that the circular perforation is located at a centre of the C-shaped female perforation; and
    a peripheral wall surrounding the C-shaped female perforation and protruding above a surface of the anchor port in order to give support to the holding means.

9. A cannula holder device having a guide for a stomach tube according to claim 8, wherein the C-shaped female perforation includes a plurality of teeth at its distal wall.

10. A cannula holder device having a guide for a stomach tube according to claim 9, wherein the first support zone includes a male protrusion that is located at a rear and upper part of the first support zone, the male protrusion including a plurality of teeth located at the rear part of the first support zone that engage with the plurality of teeth provided at the distal wall of the C-shaped female perforation of the anchor port to form a graduated tightening in order to avoid removal of the holding means and to maintain the cannula pressured.

11. A cannula holder device having a guide for a stomach tube according to claim 9, wherein the plurality of teeth located in the C-shaped female perforation have a downwardly inclination to allow only anti-clockwise rotation to avoid unwanted and regression movements of the holding means.

\* \* \* \* \*